(12) United States Patent
Burkhardt et al.

(10) Patent No.: US 8,303,912 B2
(45) Date of Patent: Nov. 6, 2012

(54) SAMPLE PICK-UP AND METERING DEVICE WITH INTEGRATED LIQUID COMPARTMENTS

(75) Inventors: Claudius Burkhardt, Lucerne (CH); Martin Burri, Bettwil (CH); Vuk Siljegovic, Mettmenstetten (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 818 days.

(21) Appl. No.: 11/502,564

(22) Filed: Aug. 10, 2006

(65) Prior Publication Data

US 2007/0036684 A1  Feb. 15, 2007

(30) Foreign Application Priority Data

Aug. 10, 2005 (EP) .................................. 05107359

(51) Int. Cl.
   *B01L 3/00* (2006.01)
(52) U.S. Cl. .......... 422/507; 422/50; 422/501; 422/502; 422/503; 422/504; 436/180
(58) Field of Classification Search ............ 422/99–101, 422/50, 501–504, 507; 222/54; 436/180
See application file for complete search history.

(56) References Cited

U.S. PATENT DOCUMENTS

| | | | |
|---|---|---|---|
| 2,737,812 A | 3/1956 | Haak | |
| 2,753,868 A * | 7/1956 | Seemar | 604/415 |
| 2,965,255 A * | 12/1960 | Gerarde | 206/220 |
| 3,045,494 A | 7/1962 | Gerarde | |
| 3,433,712 A * | 3/1969 | Gerarde | 600/576 |
| 3,603,156 A * | 9/1971 | Konkol | 73/864.02 |
| 3,640,267 A * | 2/1972 | Hurtig et al. | 600/578 |
| 3,706,306 A * | 12/1972 | Berger et al. | 600/575 |
| 3,762,540 A * | 10/1973 | Baumann et al. | 206/219 |
| 3,799,742 A | 3/1974 | Coleman | |
| 3,992,150 A * | 11/1976 | Retzer | 436/164 |
| 4,134,512 A * | 1/1979 | Nugent | 215/247 |
| 4,304,869 A * | 12/1981 | Dyke | 435/287.6 |
| 4,434,235 A | 2/1984 | Rabi et al. | |

(Continued)

FOREIGN PATENT DOCUMENTS

DE  19744550 A1  6/1998

(Continued)

OTHER PUBLICATIONS

Karl, J., Burns, G., Engel, W.D., Finke, A., Kratzer, M., Rollinger, W., Schickaneder, E., Seidel, C. "Development and Standardization of a New Immunoturbidimetric HbA$_{1c}$Assay", Klin. Lab, 1993; 39: 991-996.

*Primary Examiner* — Jyoti Nagpaul
(74) *Attorney, Agent, or Firm* — Roche Diagnostics Operations, Inc.

(57) ABSTRACT

The present invention concerns sample pick-up and metering devices, analytical test systems for determining an analyte in a sample liquid and their use for this purpose and methods for determining an analyte in a sample liquid. They comprise or use a sample pick-up and metering device according to the invention which consists of a support and a metering element integrated into the support for taking up a defined volume of sample liquid and a closed liquid compartment located on the support which contains a defined volume of a liquid where the liquid compartment on the support can be opened.

17 Claims, 3 Drawing Sheets

U.S. PATENT DOCUMENTS

| | | | |
|---|---|---|---|
| 4,459,997 A * | 7/1984 | Sarstedt | 600/577 |
| 4,990,075 A | 2/1991 | Wogoman | |
| 5,162,237 A | 11/1992 | Messenger et al. | |
| 5,272,093 A | 12/1993 | Silva et al. | |
| 5,364,533 A * | 11/1994 | Ogura et al. | 210/645 |
| 5,372,948 A | 12/1994 | Yip | |
| 5,935,864 A * | 8/1999 | Schramm et al. | 436/174 |
| 5,951,492 A * | 9/1999 | Douglas et al. | 600/583 |
| 6,159,747 A | 12/2000 | Harttig et al. | |
| 6,231,815 B1 | 5/2001 | Bainczyk et al. | |
| 6,399,293 B1 | 6/2002 | Pachl et al. | |
| 2001/0016360 A1 | 8/2001 | Carpenter | |
| 2002/0001822 A1 | 1/2002 | DiCesare | |
| 2002/0173044 A1 | 11/2002 | Pachl et al. | |
| 2003/0171699 A1 | 9/2003 | Brenneman | |
| 2003/0185710 A1 * | 10/2003 | Matsuda et al. | 422/72 |
| 2004/0191124 A1 | 9/2004 | Noetzel et al. | |
| 2005/0084982 A1 | 4/2005 | Brauner | |

FOREIGN PATENT DOCUMENTS

| | | |
|---|---|---|
| EP | 0863401 B1 | 9/1998 |
| EP | 0989407 B1 | 3/2000 |
| EP | 1018648 A1 | 7/2000 |
| EP | 1445020 A1 | 8/2004 |
| EP | 1522343 A1 | 4/2005 |
| JP | 2003 135435 | 5/2003 |
| WO | WO 93/12421 | 6/1993 |
| WO | WO96/07919 | 3/1996 |
| WO | WO96/14017 | 5/1996 |
| WO | WO2005/001487 A1 | 1/2005 |

* cited by examiner

SAMPLE PICK-UP AND METERING DEVICE WITH INTEGRATED LIQUID COMPARTMENTS

BACKGROUND OF THE INVENTION

The present invention concerns devices for picking up and metering sample liquids and analytical test systems for determining analytes in a sample liquid which, in addition to such devices for picking up and metering sample liquids, have a reaction cuvette for carrying out the reactions necessary to determine the analyte.

In addition, the invention concerns the use of such analytical test systems for determining analytes in a sample liquid and methods for determining analytes in a sample liquid in which such analytical test systems are used.

The present invention is in the field of sampling and sample metering and performing analytical tests to determine an analyte in a sample liquid. In particular, it concerns analytical test devices and methods which are suitable for detection methods that employ liquid reagents or buffers or which comprise a plurality of consecutive individual steps and reactions.

The determination of analytes in a sample liquid is of major importance in many industrial and scientific fields for example for analytical investigations of the environment and foods and also for medical and diagnostic examinations so that numerous analytical methods and test devices have been developed in the past. Many methods of determination require a plurality of consecutive analytical reactions with a variety of reagents and reaction conditions which have to be carried out successively in the form of process steps according to a fixed protocol. Usually a large number of manual process steps such as pipetting, mixing, transfer into other reactions spaces, incubation phases or centrifugation or separation steps are necessary to carry out such analytical methods which are often prone to errors and thus can lead to falsified analyte determinations. Although different test systems have been developed in the past in which it has been attempted to simplify and automate such process steps, such test systems are often still complex and thus expensive to manufacture. Furthermore, they usually require specially trained operating personnel and/or complicated and expensive laboratory equipment to carry out the analyte determination. Although it is often possible to automate a large number of process steps in such systems, the steps of sample collection, sample preparation and/or of the metered introduction of sample into the system usually still have to be carried out manually and are thus prone to errors.

Recently microfluidic test systems have been used to try to transport the applied sample through specially designed channels and chambers so that it comes into contact therewith the detection reagents at defined sites. In this process the sample liquid or the reaction mixture successively passes through a plurality of reaction, incubation and/or detection areas thus enabling a sequence of spatially and/or chronologically separated reaction steps. However, this requires devices that are very complicated to manufacture and thus expensive, and often also requires additional process steps such as dilution or mixing steps which usually have to be carried out outside of the device because such microfluidic devices can often only be equipped with dry chemistry reagents for manufacturing and stability reasons. In such microfluidic devices liquids are usually transported by means of capillary forces which in turn makes high demands on the accuracy and form of the capillary channels and consequently results in correspondingly expensive and complex manufacturing processes. Liquid transport by externally applied forces such as by centrifugation, rotation or also by pumps is usually less demanding on the test device itself but these technologies require additional costly apparatuses such as centrifuges or pumps.

Another group of analytical test elements are carrier-bound tests such as test carriers or test strips based on dry chemistry. In this case the reagents and in particular specific detection reagents and auxiliary reagents are embedded or immobilized in appropriate detection elements of a solid carrier. In the classical test strip formats all reagents are present as dry chemicals on the test strips and the reagents are only dissolved by the sample liquid and thus brought into a reactive state. However, since not all reagents are suitable for stable storage in a dry chemistry form, the application of such dry chemistry test strips is limited to detection reactions in which all reaction partners can be stored in a dry chemistry form. Also in the case of carrier-bound tests, the sample is usually applied manually by pipetting a certain sample volume or contact with a large unmetered volume of the sample liquid such as a drop of blood of undefined size. Dilution steps that may be necessary also have to be carried out manually before sample application in most test strip formats. Attempts at also storing liquid reagents on test strips also increases the complexity of their superstructural parts and thus led to less user-friendly and also more expensive test systems.

The sample pick up devices and analytical test systems described in the prior art are characterized by a complex design or a limitation to dry chemistry reagents. The manufacture and assembly of such complex test elements are, however, usually very complicated and costly. In some cases additional complex instruments are required to carry out the analyte determinations such as to centrifuge or rotate the test elements which increases the complexity of the entire analytical system and its purchase costs and thus also increases the cost per test carried out.

No devices are known from the prior art for picking up and metering sample liquids and no analytical test systems are known for determining analytes in a sample liquid which can be manufactured in the simplest possible and most cost-effective manner, operated in as simple and less error-prone manner as possible, are not limited to the use of dry chemistry reagents and which enable an exact metering and/or dilution of the sample liquid to be examined with buffer or diluent solutions or reagent solutions.

SUMMARY OF THE INVENTION

It is against the above background that the present invention provides certain unobvious advantages and advancements over the prior art. In particular, the inventors have recognized a need for improvements in sample pick-up and metering devices with integrated liquid compartments.

Although the present invention is not limited to specific advantages or functionality, it is noted that the present invention provides devices for picking up and metering sample liquids and analytical test systems for determining analytes in a sample liquid which largely avoid the said disadvantages of the existing devices in the prior art. The devices of the present invention for picking up and metering sample liquids can be manufactured and operated in the simplest possible manner, and enable the sample liquid contained in the metering element to be removed from this element and transferred into another compartment. The devices can also be operated as simply and as free of errors as possible which additionally enable the sample liquid contained in the metering element to be admixed with a diluent solution or a reagent solution in a defined dilution ratio.

The analytical test systems for determining analytes in a sample liquid can be manufactured in the simplest possible and cost-effective manner, can be operated by the user in the simplest possible manner, and allow a very exact metering and optionally dilution of the sample liquid. A combination of analytical test systems for determining analytes in a sample liquid allow the user to select and determine the desired analyte from a large number of possible analytes in a simple and cost-effective manner.

Further, the analytical test systems and methods for determining analytes in a sample liquid enable in particular multistep detection methods to be carried out in a user friendly manner with the fewest possible manual process steps and/or with the least elaborate instrumentation. The analytical test systems and methods for determining analytes in a sample liquid are not limited to the use of dry chemistry reagents.

In accordance with one embodiment of the present invention, a sample pick-up and metering device is provided which comprises a metering element for picking up a defined volume of the sample liquid, and a support which contains at least one closed liquid compartment in which a defined volume of a liquid is contained, wherein the metering element is an integrated component of the support and the liquid compartment on the support can be opened.

In accordance with another embodiment of the present invention, an analytical test system for determining an analyte in a sample liquid is provided comprising a sample pick-up and metering device and a reaction cuvette. The sample pick-up and metering device comprises a metering element for picking up a defined volume of the sample liquid, and a support which contains at least one closed liquid compartment in which a defined volume of a liquid is contained. The metering element is an integrated component of the support and the liquid compartment on the support can be opened.

In accordance with yet another embodiment of the present invention, a method for determining an analyte in a sample liquid using the analytical test system defined directly above is provided comprising: a) contacting the metering element with the sample liquid to be analysed such that a defined volume of sample liquid remains in the metering element, b) introducing the sample pick-up and metering device into the reaction cuvette, c) opening at least one liquid compartment on the support such that the liquid contained in this liquid compartment flows into the reaction cuvette and comes there into contact with the sample liquid contained in the metering element in such a manner that the sample liquid from the metering element is provided in the reaction cuvette and a reaction mixture is formed, and d) determining the analyte on the basis of a characteristic measured quantity for the analyte. Optionally, the method can further comprise adding reagents for the determination of the analyte and/or intermixing the reaction mixture.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

The following list of reference numerals can be used to better understand the figures:

| | |
|---|---|
| 1 | sample pick-up and metering device |
| 4 | foil |
| 5 | liquid compartment |
| 6 | discharge tongue |
| 7 | support |
| 8 | metering element |
| 9 | recess |
| 11 | reaction cuvette |
| 12 | analytical test system |
| 17 | first dry chemistry reagent |
| 18 | detection device |
| 19 | second dry chemistry reagent |

DETAILED DESCRIPTION OF THE INVENTION

The inventive integration of a metering element and at least one openable liquid compartment which contains a defined volume of a liquid, in a common support enables for the first time a sample pick-up and metering device to be provided which combines the devices and materials employed to pick up, meter and provide the sample liquid to be examined in a single constructional unit. This now allows especially a simple and cost effective manufacture of such sample pick-up and metering devices on an industrial scale. Furthermore, the integration into a constructional unit allows a simple operation of these devices according to the invention by the user since they combine all devices and functions that are employed to pick-up and meter the sample liquid as well as to provide the sample liquid metered in this manner for subsequent purposes. Such devices are particularly suitable for use in analytical test systems since the device according to the present invention enables the user to pick-up a defined volume of sample liquid and provide it in a compartment designated for the further analyte determination. In particular, the device according to an embodiment of the invention allows the sample liquid to be mixed with a defined volume of the liquid contained in the liquid compartment and thus to make a defined dilution of the sample liquid and/or to add reagents. The integration according to the invention of the metering element with the liquid compartment on a common support enables defined reaction mixtures to be provided for an analyte determination in a simple manner and in a few process steps which are the basis for determining the analyte in a manner that is as exact and free of errors as possible. In particular, the use of the sample pick-up and metering devices according to the invention enables a substantial standardization and/or automation of the steps of sample pick-up and metering, sample dilution and transfer into a reaction compartment which otherwise would have to be carried out manually, for example by pipetting, which in turn can considerably increase the accuracy and reproducibility of these steps and thus also of subsequent analyte determinations.

In accordance with the various embodiments of the present invention, the sample pick-up and metering devices comprise a support which contains at least one metering element and a liquid compartment as integral components. The support can be designed to meet the special requirements of the respective intended use. Thus, the support can have other optional devices which improve the handling of the sample pick-up and metering device or which enable it to be implemented in an analytical test system. For example, the support can have grip mouldings or marks or guiding or attachment elements such as, for example, grooves, slots or locking connections for implementation in an analytical test system. If the device according to the invention is to be used in an automated manner, the support can have devices for this such as guiding or catching elements which enable the support or individual parts of the support to be moved by an instrument in order to for example open the liquid compartment. The support can also comprise optional identification elements such as alphanumerical numerals, bar codes, two-dimensional codes or RFID transponders. This enables support-specific data for example on the type and size of the metering element or volume and composition of the liquid contained in the liquid compartment or data such as expiry dates, lot numbers or calibration information to be transmitted to the user or to a reading unit on an instrument.

According to an embodiment of the present invention, the support comprises at least one closed liquid compartment which contains a defined volume of a liquid and which can be opened. The liquid compartment as a component of the support can for example be designed as a subarea of the support itself, for example as an indentation of an otherwise substantially planar support. This can be filled with a defined volume of a liquid and subsequently sealed liquid-tight with a cover layer so that a closed liquid compartment is present on the support. Such indentations on a support can be designed and manufactured using a wide variety of methods known to a person skilled in the art depending on the material that is used, for example by means of injection moulding or deep drawing processes. Such indentations can be filled with a defined volume of a liquid for example by means of the fact that the geometry of the indentation itself defines the volume contained therein or a metered volume of a liquid is placed in the indentation. In order to obtain a closed liquid compartment this indentation is sealed liquid-tight after it has been filled with liquid. This can be achieved by applying a cover layer, for example a liquid-tight and gas-tight plastic or metal foil. Other embodiments of a liquid compartment on a support can be found among others in U.S. Pat. No. 5,272,093. In addition to such liquid compartments integrated directly into the support, it is also possible to provide liquid compartments that contain a defined volume of a liquid and are initially closed and to join them to the support in an additional manufacturing step, for example by locking in position or gluing. Such embodiments of a liquid compartment on a support can be found among others in EP 0863401 in which methods and possible materials are described for manufacturing liquid-filled blisters made of plastic-coated aluminium foil and their combination with dry chemistry test strips. In addition to such liquid-filled blisters, it is also possible to use other closed liquid compartments such as glass or plastic ampoules which are attached to the support. A property of the liquid compartments is that they can be opened to specifically release the liquid contained therein. The liquid compartment can be opened using different methods and devices which depend in particular on the material and methods by which the liquid compartment is sealed.

In a typical embodiment, the liquid compartment is closed by a detachable or pierceable liquid-tight and gas-tight foil. This foil can then be pulled off or pierced to open the liquid compartment and release the liquid contained therein. For example, the liquid compartment can be closed by a cover foil that is glued or welded on such as a liquid-tight and gas-tight plastic or metal foil which is glued on or welded onto the support in the area of the indentation of the liquid compartment. The foil can be removed manually or with the aid of an instrument to release the liquid contained therein as described for example in U.S. Pat. No. 5,272,093. Other methods of opening are for example to pierce the cover foil or other surfaces bordering the liquid compartment with a device or design of the support for example in the form of a pointed tip in the support. Such methods are described for example in EP 0863401.

Another inventive component of the support is an integrated metering element to pick-up a defined volume of a sample liquid. The metering element can either already be integrated during the manufacture of the support or not until a later manufacturing step. In the former case this can be carried out in the case of supports made of plastic that are manufactured in an injection moulding process, by moulding a metering function during the injection moulding as a particular moulded area of the support for example in the form of a metering capillary or of a metering channel. In the latter case this can for example be carried out by firstly providing a metering element in the form of a separate constructional element which is joined with the support in a subsequent manufacturing step, for example glued onto the support or moulded into the support material in an injection moulding process. In principle any constructional element which serves to store and/or meter defined liquid volumes can be regarded as a metering element in the sense of the present application. These constructional elements are characterized by their geometric dimensions and structures designed for this purpose such as capillary channels or openings with characteristic dimensions and diameters which take up a defined volume of a liquid and can make it available again for further use. Metering elements can also be realized as microstructures and in particular be manufactured from semi-conductors, plastics, glass, ceramics or metals.

In a typical embodiment of the device according to the invention the metering element is designed as a capillary or channel. Examples of such metering elements are known from U.S. Pat. No. 3,799,742 or U.S. Pat. No. 5,162,237, which describe metering elements in the form of a metering capillary or metering channel or metering notch. However, in addition to these typical embodiments, other embodiments of a metering element known to a person skilled in the art are also possible for example in the form of absorbent materials such as fleeces or sponge-like materials which can take up and release a certain volume of liquid. Such embodiments are described for example in DE 19744550. In addition to untreated liquids such as untreated blood samples, it is also possible to use already pretreated liquids as a sample liquid that can be taken up by the metering element within the scope of the present application such as blood samples that have been admixed with anticoagulants or other reagents and/or diluted blood samples.

In another typical embodiment of the sample pick-up and metering device according to the invention at least one liquid contained in the liquid compartment is a buffer or diluent solution. This is then particularly advantageous when the sample liquid taken up in the metering element has to be firstly diluted in a defined dilution ratio in subsequent process steps in order to subsequently carry out analytical determinations with this diluted sample liquid. For this purpose a defined volume of a buffer or diluent solution is placed in at least one liquid compartment of the support which, after opening this liquid compartment, comes into contact with the defined volume of sample liquid contained in the metering element of the support and mixes with this sample liquid in a defined dilution ratio. Thus, for example, a dilution ratio of 1:200 can be achieved when the metering element of the support can take up a volume of 5 µl sample liquid and the liquid compartment of the support contains a volume of 995 µl of a buffer or diluent solution. In principle all liquids can be used as buffer or diluent solutions which are miscible with the sample liquid and ensure a substantially homogenous distribution of the sample liquid in the dilution mixture that is formed. In particular, water or aqueous solutions that contain stabilizing inorganic or organic buffer substances and/or salts can be used as buffer or diluent solutions. Buffer or diluent solutions usually contain no substances that specifically interact or react with components of the sample solution and in particular with sample components that are to be analysed. Examples of these are physiological saline solution, Ringer's solution or organic buffer solutions such as HEPES (2-[4-2-hydroxyethyl)piperazino]ethane sulfonic acid) buffer.

In a further typical embodiment of the sample pick-up and metering device according to the invention at least one liquid contained in the liquid compartment is a reagent solution. This is especially advantageous when the sample liquid has to for example be admixed with reagents to form a reaction mixture to carry out analyte determinations. For this purpose a defined volume of a reagent solution can be placed in at least one liquid compartment of the support which, after opening this liquid compartment, comes into contact with and is mixed with the defined volume of sample liquid contained in the metering element of the support so that the reaction mixture is prepared for the analyte determination. In this case the reagent solution can contain all or also only individual reagents and optionally other auxiliary substances employed to determine an analyte in a sample liquid. A person skilled in the analytical field knows such analyte-specific reagents and auxiliary agents. In the case of analytes that are to be determined enzymatically these may for example be enzymes, enzyme substrates or indicators; in the case of immunological detection methods they may be specific binding partners of the analyte such as antibodies or antigens or in the case of optical or electrochemical detection methods they may be for example dyes or electrochemical mediators.

In other typical embodiments of the sample pick-up and metering device according to the invention the support contains several liquid compartments that are separate from one another. In particularly typical embodiments these liquid compartments can be opened simultaneously or sequentially. In this case the liquid compartments can contain identical or different liquids. Embodiments in which identical liquids are present in several liquid compartments can for example be used to dilute the sample liquid in several steps. For this purpose a first liquid compartment which contains a first defined volume of a liquid can be firstly opened as a result of which the sample liquid is initially diluted with this first liquid volume. If one now finds that the concentration of the analyte in the liquid sample is still too high for a reliable determination, a second liquid compartment which contains a second defined volume of a liquid can be opened in a second dilution step resulting in another dilution of the liquid sample. Thus the liquid sample can be successively diluted. For example, such a device according to an embodiment of the invention which has a metering element that can hold 10 µl sample liquid, a first liquid compartment which contains 90 µl of a liquid and a second liquid compartment which contains 900 µl of a liquid can be used to dilute the sample liquid firstly in a ratio of 1:10 by opening the first liquid compartment and finally in a ratio of 1:100 by additionally opening the second liquid compartment. In further embodiments the liquids contained in the liquid compartments can be at least partially different. Such embodiments are especially advantageous when different reagents have to be added to the sample liquid. These reagents can be present in a wet-chemistry form in the respective compartments and be added by the device according to the invention successively or also simultaneously to the sample liquid by opening the respective liquid compartments. A simultaneous opening of several liquid compartments is for example advantageous when reagent liquids should be added to the sample liquid which react undesirably with one another if their ingredients were to be stored together. By dividing the ingredients among several liquid compartments according to an embodiment of the invention they can, on the one hand, be stored in a stable manner uninfluenced by one another and, on the other hand, also be simultaneously added to the sample in one operation step by simultaneously opening the liquid compartments. The liquid compartments in such embodiments are particularly advantageously arranged next to one another and closed by a common cover foil which can be pulled off in an upwards movement in a uniform operating step such that all liquid compartments that are closed by it are simultaneously opened. In contrast, a sequential opening of the liquid compartments is especially advantageous when multistep detection reactions are employed to determine the analyte. In such embodiments the liquid compartments are particularly advantageously arranged on top of one another and are closed by a common cover foil which is firstly pulled upwards by a certain distance in a first step so that firstly the liquid compartment at the bottom can be opened for a sequential opening of the liquid compartments and subsequently is pulled upwards by a further distance in a second step so that the liquid compartment that is further above can be opened. Further liquid compartments can be contained on the test support according to an embodiment of the invention in an analogous manner which contain additional reagent solutions for additional reaction steps. A combination of one or more liquid compartments which contain buffer or diluent solutions with one or more liquid compartments which contain reagent solutions is also possible on a support according to the invention.

Another aspect of the present invention is the provision of analytical test systems for determining an analyte in a sample liquid which comprise an inventive sample pick-up and metering device according to the previous embodiments and additionally a reaction cuvette.

By combining at least one such sample pick-up and metering device with a reaction cuvette it is possible according to the invention to provide an analytical test system which can be manufactured simply and economically, can be operated in a simple and substantially error-free manner by the user and enables a metering and dilution of sample liquid which is as exact as possible. Furthermore, the use according to the invention of at least two different components (sample pick-up and metering device and reaction cuvette) in the analytical test systems enables a modular use of a common component for all analytes to be determined and a specific component for the respective analyte. This allows analytical test systems to be combined according to the building block principle which allow the user to select and determine the desired analyte from a large number of possible analytes in a simple and economic manner. In particular, the analytical test systems according to the invention also enable multistep detection reactions for analyte determinations to be carried out with the fewest possible process steps that have to be carried out manually or with less complicated instrumentation and which are in particular not limited to the exclusive use of dry chemistry reagents. By combining at least one sample pick-up and metering device according to the various embodiments of the present invention with a reaction cuvette a test system is provided which can be manufactured and operated in a simple manner and which can comprise all consumables and reagents employed for the analyte detection. The use of such an analytical test system enables the process steps of sample pick-up, metering and sample provision, sample dilution and the addition of reagents to the sample and performing the reactions employed for analyte detection to take place in one reaction space.

The reaction space of the analytical test system is formed according to an embodiment of the invention by a reaction cuvette in which the sample liquid picked up in the metering element and a liquid contained in a liquid compartment of the support and optionally other reagents can be brought together and mixed. The reaction cuvette additionally serves as a reaction space in which at least some of the reactions employed to detect the analyte can be carried out. The reaction cuvette can have many geometric shapes. In addition to the classical cuvette shapes such as rectangular or round cuvettes, the cuvette shapes can be adapted to the design of the support or the detection method that is used. The reaction cuvette can optionally contain other compartments. These compartments can have other functions and for example serve as fluidic paths, to separate certain sample or reagent components, to further dilute the reaction mixture, as reagent and mixing chambers or reaction spaces, as detection cuvettes or as waste spaces. Examples of such more complex embodiments are described for example in EP 1445020, U.S. Pat. No. 4,990,075 or U.S. Pat. No. 5,162,237 in the form of fluidic test modules and cassettes. Also such more complex embodiments which in addition to combining metered amounts of sample liquid and another liquid and carrying out at least some of the detection reactions, additionally fulfil other functions, are regarded as reaction cuvettes within the scope of the present application. In this connection the reaction cuvettes can in principle consist of any material which does not significantly adversely affect the reactions that enable the analyte determination by for example binding the analyte or interacting with detection reagents or solvents involved in the reaction. In the case of optical detection methods, transparent reaction cuvettes or reaction cuvettes which have at least a transparent subarea for detecting the analyte are particularly suitable. Such cuvettes can be composed in particular of glass and transparent plastics. If, for example, electrochemical detection methods are used to detect the analyte, the reaction cuvette can advantageously consist of insulating materials such as plastic or glass. Like the support, the reaction cuvette can be designed to meet the particular requirements of the respective intended use and for example have optional devices which improve the handling of the reaction cuvette or its interaction with other components such as the support. In particular, the reaction cuvette can have guide or attachment elements such as, for example, grooves, slots or locking connections to hold and fix the support. If it is intended to also use the test system according to the invention in an automated manner, the reaction cuvette can have devices for this such as guide or attachment elements which enable the reaction cuvette and thus the entire analytical system according to the invention to be gripped and moved by an instrument, for example by an analyser. Furthermore, the reaction cuvette, like the support, can contain identification elements and/or grip mouldings.

In order to carry out the reactions which enable the analyte detection, in accordance with an embodiment of the present invention, the metering element integrated on the support is firstly brought into contact with the sample liquid to be examined such that a defined volume of sample liquid is taken up in the metering element and remains in this element. In a next step the support is introduced into the reaction cuvette such that the metering element is located within the reaction cuvette. In a further step at least one liquid compartment located on the support is opened such that the liquid contained in this liquid compartment flows into the reaction cuvette. The amount of this liquid is of such a magnitude that the liquid comes into contact with the sample liquid contained in the metering element. As a result the sample liquid located in the metering element is at the same time diluted and provided for the detection reactions that occur in the reaction cuvette as also described for example in U.S. Pat. No. 5,162,237. If the liquid contained in the liquid compartment of the support contains reagents, they are also added to the sample liquid in this process step to form the reaction mixture necessary to start the detection reactions. Optionally, it is possible to carry out further process steps such as adding additional reagents necessary to determine the analyte and/or mixing this reaction mixture. In a final step a characteristic measurable variable of the reaction mixture is determined with the aid of a detection device from the magnitude of which the concentration of the analyte in the sample liquid can be deduced.

In another embodiment, the analytical system according to the invention additionally contains a mixing device. Mixing the liquids present in the reaction cuvette can ensure that the sample liquid contained in the metering element is released as completely as possible since an intermixing of the sample liquid contained in the metering element with the liquid released from the liquid compartment of the support to form a reaction mixture is not based alone on diffusive processes and is considerably accelerated by the mixing movement. A very homogenous distribution of the sample liquid and thus of the analyte in the reaction mixture is thereby also achieved which is advantageous for the analyte determination. The intermixing can take place by moving the reaction cuvette or the entire analytical test system for example by swinging or shaking which can be carried out manually or also by means of instrumentation. The intermixing can also be carried out by mixing devices such as paddle mixers or magnetic stirrers. In a particularly typical embodiment the reaction mixture is intermixed by means of magnetic stirrers in which a magnetic stirring bar is present in the reaction cuvette as a mixing device. This stirring bar can already be present in the reaction cuvette before introducing the support or before opening the liquid compartment located on the support and for example be already packaged together with the reaction cuvette. In other embodiments a magnetic stirring bar can be placed in the reaction cuvette as a mixing device when the liquid compartment located on the support is opened or afterwards. This can be achieved by placing a magnetic stirring bar together with the liquid in a liquid compartment whereupon the stirring bar gets into the reaction cuvette together with the liquid of the opened liquid compartment by opening the liquid compartment for example by removing a cover foil.

In another typical embodiment the analytical system according to the invention contains devices which enable the analyte to be determined in the reaction cuvette. These devices are essentially detection devices in the reaction cuvette or designs of the reaction cuvette which enable a measurable variable that is characteristic for the analyte to be determined. For this purpose it is not, however, necessary for all devices employed in determining the analyte to be present in the reaction cuvette but rather it is sufficient that some of the devices are present in the reaction cuvette or the reaction cuvette is designed accordingly so that a characteristic measurable variable for the analyte can be determined on the reaction mixture present in the reaction cuvette. If the analyte is determined by means of optical methods such as colorimetric, photometric, turbidimetric, spectral photometric, fluorescence- or luminescence-optical, fluorescence-polarization optical or infrared and raman-spectrocopic methods, at least subareas of the reaction cuvette must be transparent to enable determination of the optical properties of the reaction mixture. For this purpose the entire reaction cuvette can consist of transparent material or only certain subareas of the cuvette can be designed to be transparent for example in the form of measuring windows. Also such embodiments of the reaction cuvette are regarded within the scope of the present application as devices which enable the determination of the analyte in the reaction cuvette. If the analyte is determined by means of electrochemical methods such as potentiometric, amperometric, coulometric or conductometric methods, the reaction cuvette must contain appropriate electrodes as detection devices on which the electrochemical detection reactions proceed and/or which serve to detect the electrochemical changes in the reaction mixture. If the analyte determination is carried out by means of other detection methods, detection devices known to a person skilled in the art for this purpose can be present in the reaction cuvette. Parts of the detection devices employed in analyte determination can also be present outside of the test system according to the invention for example in the form of a detection unit as a component of an analyser into which the analytical test element according to the invention is inserted to carry out and/or evaluate the analyte determination. In the case of optical detection methods such a detection unit can for example contain light sources, filters and light detectors, in the case of electrochemical detection methods it can for example contain connections for contacting the electrodes located in the reaction cuvette, voltage sources and measuring instruments to detect the electrical parameters. Such an analyser may additionally contain devices for further processing the primary measurable variables determined in this manner into the desired values of analyte concentrations and devices for transmitting or displaying these values.

The use according to the invention of at least two different components (sample pick-up and metering device and reaction cuvette) in the analytical test systems enables a modular use of a standard component for all analytes to be determined and a specific component for the respective analyte. This inventive solution thus provides a versatile modular analytical system for a large number of different analytes which is nevertheless economic to manufacture and simple to handle. Furthermore the integration of the reagents necessary for the analyte determination in one component of the analytical test system according to the invention enables different analyte determinations to be carried out in a simple and thus less error-prone manner.

In a first typical embodiment this is achieved in that the specific reagents employed in determining the analyte are contained in the form of reagent liquids in one or more liquid compartments on the support of the sample pick-up and metering device. This allows the use of a universal reaction cuvette that is standardized for all tests into which the respective specific support containing the corresponding specific reagents for the respective analyte determination is placed. This allows the user to rapidly and flexibly carry out analyte-specific tests by choosing the appropriate support. In a typical embodiment several liquid compartments are present on the support which contain different reagent liquids and which can be opened at different times so that the reagent liquids contained therein can be added to the reaction mixture at different times thus enabling sequential detection reactions to be carried out. Thus, for example, by opening a first liquid compartment, a first reagent solution can be placed in the reaction cuvette which comes into contact there with the sample liquid contained in the metering element and forms a reaction mixture with this sample liquid in which a first detection reaction takes place. By opening a second and optionally other liquid compartments it is now possible to introduce a second and optionally other reagents solutions into the reaction cuvette and to mix them there with the previous reaction mixture. In this manner the reagents contained in these reagent liquids are added to the reaction mixture so that a second and optionally other detection reactions can now take place. This enables analyte determinations with sequential detection reactions to be carried out in a simple, user-friendly and less error-prone manner. In further embodiments the sample liquid contained in the metering element can firstly be provided by opening a liquid compartment on the support which contains a buffer or diluent solution without analyte-specific reagents. In this embodiment the reagents employed for the analyte determination are added by subsequently opening one or more liquid compartments on the support which contain reagent solutions with the employed reagents. The different liquid compartments can be opened by the user who for example manually opens the respective liquid compartments of the support at certain times so that defined sequences of reagent additions and reaction times can be adhered to. In a typical embodiment the different liquid compartments are opened by a mechanical device that is appropriately controlled and which automatically opens the respective liquid compartments on the support at certain times thus also enabling complex sequential detection reactions to be carried out in a defined and exact manner without error-prone manual steps. This can for example be realized by arranging several liquid compartments on the support above one another and closing them by a common cover layer, for example a sealing foil. This foil can contain shapes where such an instrument mechanism can engage. These can for example be lugs of the sealing foil which can be gripped and held by such a mechanism. This cover layer can now for example be pulled off upwards in a stepwise manner by a certain distance by appropriate actuation of the instrument mechanism in order to sequentially open the liquid compartments such that the liquid compartment at the bottom can be firstly opened and then successively the overlying liquid compartments can be opened. Such a controllable instrument mechanism for opening the liquid compartments on the support can be a component of the analytical instrument in which the analytical test system according to the invention can be used in order to carry out the analyte determination.

In a second typical embodiment this is achieved by the fact that the specific reagents employed in determining the analyte are present in the reaction cuvette. This enables a universal sample pick-up and metering device to be used that is standardized for all tests and has one or more liquid compartments for preparing and diluting the sample liquid in the reaction cuvette where said compartments contain a universal buffer or diluent solution. The use of such a universal buffer or diluent solution which contains no analyte-specific reagents enables the use of a single embodiment of the sample pick-up and metering devices for many different analyte determinations since the specificity of the analyte determination is introduced by the respective specific reaction cuvettes containing the appropriate reagents. This enables the user to rapidly and flexibly carry out an analyte-specific test by selecting the appropriate reaction cuvette. In this case the reagents can be present in the reaction cuvette as liquid reagents. However, in a particularly typical embodiment the reagents are present in the reaction cuvette in a dry chemistry form. In this case the reagents can be present in various dry chemistry forms for example as powders, in tablet form or in support matrices such as impregnated on paper or fleeces. In this case the specific reagents employed in determining the analyte can be present in the form of a common reagent spot in the reaction cuvette or be distributed over different reagents spots in the reaction cuvette which can be simultaneously or successively contacted by the reaction mixture and thus be brought into a reactive form. A distribution of the dry chemistry reagents over several areas of the reaction cuvette with simultaneous contacting and dissolution by the reaction mixture is particularly suitable when using dry chemistry reagents that can react with one another in an undesired manner but should be simultaneously added to the reaction mixture. A distribution of the dry chemistry reagents over several areas of the reaction cuvette with sequential contacting and dissolution by the reaction mixture is especially suitable for analytical methods with sequential detection reactions. Thus, for example, the reaction mixture can come into contact and react with a first dry chemistry reagent in a first position of the analytical test system, then the reaction mixture is moved to a second position in which the reaction mixture comes into contact with a second dry chemistry reagent and the next step of the detection reaction can take place by moving the analytical test system or by further addition of a buffer or diluent solution. This applies similarly to other reaction steps. Such test systems are described for example in U.S. Pat. Nos. 4,990,075, 5,162,237 and 5,372,948. The test system can be moved by an external instrument device which is for example a component of an analyser and, by means of an appropriate control, ensures an exact transport of the reaction mixture to the respective reagent spots at defined times enabling the reaction sequence and incubation times to be exactly adhered to. In other embodiments it is also possible that the individual areas of the reaction cuvette on which dry chemistry reagents are positioned are arranged above one another so that firstly the lowest reagent spot is contacted by adding a first volume of a liquid by opening a first liquid compartment on the support. The liquid level of the reaction mixture in the reaction cuvette can now be raised by adding a second and optionally other volumes of a liquid by opening a second and optionally further liquid compartments on the support as a result of which the overlying reagent spots can now also be contacted by the reaction mixture such that the reagents contained therein can be released. In other embodiments an at least temporary rise in the liquid level of the reaction mixture and thus the possibility of contacting other reaction spots can for example be achieved by intensified stirrer movements.

In other embodiments combinations of the two aforementioned embodiments are also possible in which for example the reagents employed in the analyte detection are divided among reagent liquids which are present in liquid compartments on the support and among dry chemistry reagents which are present in the reaction cuvette.

Another aspect of the present invention concerns the use of an analytical test system according to the invention to determine an analyte in a sample liquid by means of sequential detection reactions and in particular to determine haemoglobin A1c (HbA1c) in a blood sample.

HbA1c is understood as haemoglobin A which is present with glycated glucose on the N-terminal valine residues of the beta chains. The determination of haemoglobin A1c allows a retrospective estimation of the average glucose concentration of the past weeks and thus the quality of the metabolic control of a diabetic. HbA1c is usually stated as a percentage of total haemoglobin for which the haemoglobin concentration is also determined in addition to the HbA1c content from the same blood sample. HbA1c has previously been mainly determined in large stationary central laboratory instruments which are often complicated to operate and thus prone to errors and cause high costs. The use of the analytical test systems according to the various embodiments of the present invention to determine HbA1c now enables such tests to be economically carried out with as little user interaction as possible and with less complicated instrumentation. Several methods are known for determining HbA1c which are described for example in EP 0989407 and EP 1445020.

The analytical test systems according to the invention can for example be used to determine HbA1c by means of immunological methods in a simple and economic manner. The immunological determination of glycated haemoglobin is described among others in Klin. Lab. 39, 991-996 (1993). In this method the HbA1c of the sample reacts with HbA1c antibodies in a first reaction step. Since the HbA1c-specific epitope occurs only once in each beta chain of glycated haemoglobin, no aggregation of the antigen-antibody complex occurs. Only when a polyhapten that has several HbA1c-specific epitopes is added, do the molecules react with the excess antibodies from the first reaction and to form an insoluble immune complex. This complex can be measured turbidimetrically. The tubidimetric signal is inversely proportional to the concentration of glycated haemoglobin in the sample. Since this method comprises several process steps, it has previously been primarily carried out in specialized analytical laboratories. The use of the analytical test system according to the invention now enables such a determination to be also carried out decentrally in a simple and economic manner. For this purpose a sample pick-up and metering device can for example be used which, in a first liquid compartment, contains a first reagent solution which contains a HbA1c-specific antibody and optionally other reagents such as PEG, surfactants, buffers and stabilizers. A second liquid compartment contains a second reagent solution which contains a HbA1c polyhapten and optionally other reagents such as PEG, surfactants, buffers and stabilizers. Optionally a haemolysing reagent can be present in a further liquid compartment which, when directly using a blood sample as a sample liquid, lyses the erythrocytes contained therein and thus releases the haemoglobin contained therein in order to determine HbA1c in the reaction mixture. This haemolysis step can, however, also be optionally carried out as a sample preparation step outside of the analytical test system according to the invention.

The performance of a HbA1c determination with such an analytical test system according to the invention is described as an example in the following:

1 µl of a haemolysed blood sample is taken up and metered by means of the metering element of the sample pick-up and metering device according to an embodiment of the present invention. The sample pick-up and metering device is now introduced into a reaction cuvette in order to carry out the detection reactions and the first liquid compartment of the support is opened which comprises 250 µl of a first reagent solution which contains a HbA1c-specific antibody. As a result the first reagent solution contained therein passes into the reaction cuvette and comes into contact with the sample liquid in the metering element thus providing the sample liquid from the metering element in the reaction cuvette. An immunological reaction now takes place in this reaction mixture as a first detection reaction between the HbA1 c of the sample liquid and the HbA1c-specific antibody of the reagent solution in which the HbA1c molecules that are present bind to the antibodies. By opening the second liquid compartment of the support which contains 50 µl of a second reagent solution which contains a polyhapten comprising several HbA1c-specific epitopes, the second reagent solution passes into the reaction cuvette and comes into contact with the reaction mixture. A second detection reaction thus occurs in which the HbA1c-specific epitopes of the polyhapten bind to the HbA1 c antibodies of the reaction mixture that are not yet occupied. As a consequence insoluble immune complexes are formed which are determined in an optically transparent and geometrically defined area of the reaction cuvette which is suitable for optical detection and, for example, is designed as a detection window, by turbidimetric measurements at a suitable wavelength, for example at 340 nm. This characteristic measured optical quantity determined in this manner is a measure for the concentration of the immune complexes in the reaction mixture. This is in turn inversely proportional to the amount of HbA1c in the blood sample because only the binding sites of the antibodies that are not occupied by HbA1c can react with the polyhapten in the second reaction step. Thus it is possible to determine the concentration of HbA1c in the blood sample by the turbidimetric determination of the immune complexes with a known volume of the liquids involved in the reaction. Optionally the HbA1c value can be related to the total haemoglobin concentration and expressed in the form of the HbA1c percentage of total haemoglobin. In a particularly typical embodiment a mixing device in the reaction cuvette enables a more rapid provision of the sample liquid and a better intermixing of the reaction mixture as well as more reliable turbidimetric measurements.

Another aspect of the present invention concerns methods for determining an analyte in a sample liquid using an analytical test system according to an embodiment of the present invention. This method comprises the steps a) contacting the metering element with the sample liquid to be analysed such that a defined volume of sample liquid remains in the metering element, b) introducing the sample pick-up and metering device into the reaction cuvette, c) opening at least one liquid compartment on the support such that the liquid contained in this liquid compartment flows into the reaction cuvette and comes there into contact with the sample liquid contained in the metering element in such a manner that the sample liquid from the metering element is provided in the reaction cuvette and a reaction mixture is formed, and d) determining the analyte on the basis of a characteristic measured quantity for the analyte.

Optionally, the method can further comprise adding reagents for the determination of the analyte and/or intermixing the reaction mixture. Optical detection methods can be employed in determining the analyte.

In order that the invention may be more readily understood, reference is made to the following examples, which are intended to illustrate the invention, but not limit the scope thereof.

Figure 1:
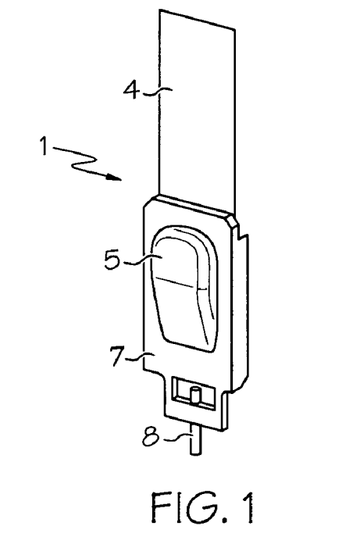
FIG. 1 shows a view of an embodiment example of a sample pick-up and metering device according to the invention which has a liquid compartment.

FIG. 1 shows a view of an embodiment example of a sample pick-up and metering device (1) according to the invention which has a liquid compartment (5). The sample pick-up and metering device (1) consists of a support (7) which has a liquid compartment (5) which in this case is designed in the form of an indentation of the support (7) and contains a defined volume of a liquid. The indentation in the present case is shaped such that it becomes flatter towards the bottom to ensure that the liquid contained therein can be completely discharged. This indentation of the support (7) is sealed by a foil (4) after it has been filled with the liquid so as to form a closed liquid compartment (5). This foil (4) can extend upwards beyond the support (7) such that it can be pulled off upwards manually or with instrument devices in order to open the liquid compartment (5). A metering element (8) is also integrated into the support (7) which is in this case in the form of an integrated metering capillary which can pick-up a defined volume of a sample liquid.

Figure 2:
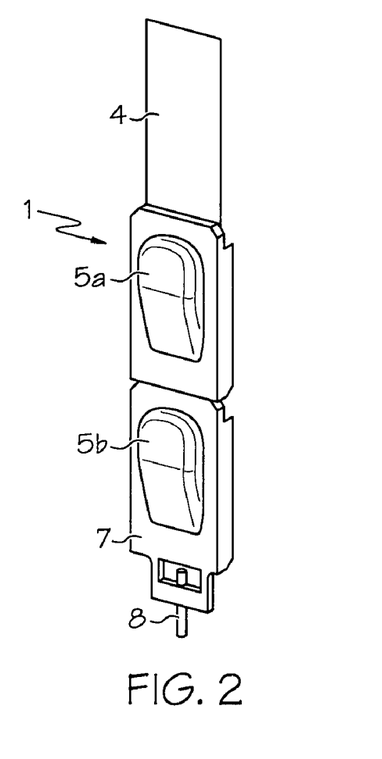
FIG. 2 shows a view of an embodiment example of a sample pick-up and metering device according to the invention which has two liquid compartments.

FIG. 2 shows a view of an embodiment example of a sample pick-up and metering device (1) according to the invention which has a first liquid compartment (5a) and a second liquid compartment (5b). The sample pick-up and metering device (1) consists of a support (7) on which the liquid compartments (5a) and (5b) are formed each in the form of an indentation of the support (7) and which each contain a defined volume of a liquid. These indentations of the support (7) are sealed by a common foil (4) after being filled with the respective liquid to thus form two closed and separate liquid compartments (5a) and (5b). The foil (4) can extend upwards beyond the support (7) so that it can be pulled off upwards manually or with instrument devices in order to open the liquid compartments (5a) and (5b). A metering element (8) is additionally integrated into the support (7) which in this case is in the form of an integrated metering capillary which can pick-up a defined volume of a sample liquid.

Figure 3A:
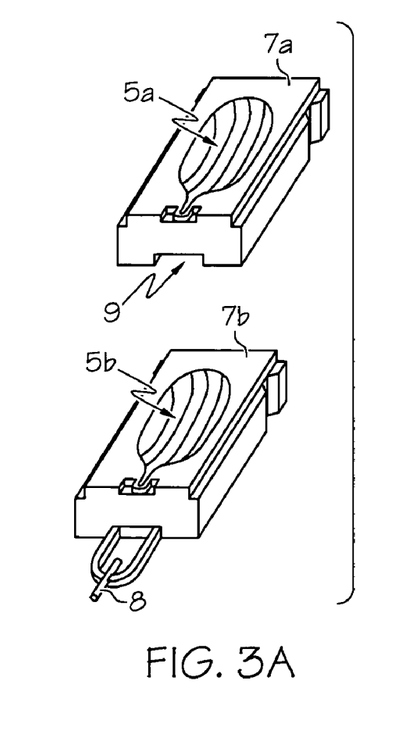
FIGS. 3A-B show views of a further embodiment example of a sample pick-up and metering device according to the invention which has two liquid compartments.
Figure 3B:
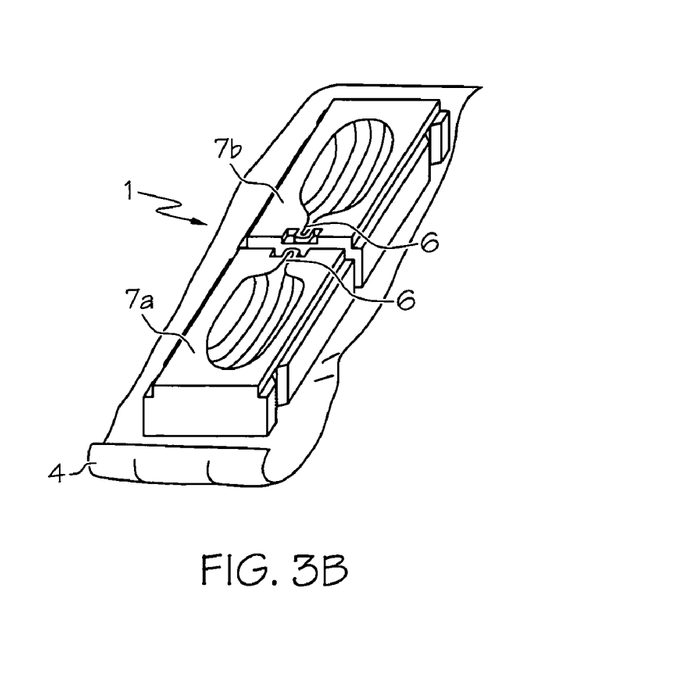

FIGS. 3A and 3B show views of another embodiment of a sample pick-up and metering device (1) according to the invention which has two liquid compartments (5a) and (5b). In this embodiment the sample pick-up and metering device (1) consists of a first support part (7a) and a second support part (7b) which are connected together by at least a common foil (4). The two support parts (7a) and (7b) can be designed as separate members (see, e.g., FIG. 3A) or be connected together (see, e.g., FIG. 3B) even without a foil (4). Thus the two support parts (7a) and (7b) can for example be manufactured as a common injection moulded part in which the two parts are firstly connected together by a thin bar. One support part, which in the case shown is the second support part (7b), has a metering element (8) which is integrated into the second support part (7b) in the form of a metering capillary and which can pick-up a defined volume of a sample liquid. Optionally the other support part, which in the case: shown is the first support part (7a), can have a recess (9) in which the metering element (8) is accommodated in the assembled sample pick-up and metering device (1). The first support part (7a) additionally has a first liquid compartment (5a) and the second support part (7b) has a second liquid compartment (5b) each in the form of an indentation. In the present case the indentation is equipped with a discharge tongue (6) that runs out flat to ensure that the liquid contained therein can be completely discharged. These indentations are sealed by a common foil (4) after being filled with the respective liquid such that closed and separate liquid compartments (5a) and (5b) are each formed on the respective support parts (7a) and (7b). In the example shown the support parts (7a) and (7b) are arranged such that the discharge tongues (6) of the two liquid compartments (5a) and (5b) are arranged opposite to one another and the metering element (8) integrated into the second support part (7b) engages in the recess (9) of the first support part (7a). By this means a sample pick-up and metering device (1) can be provided by bringing together the two support parts (7a) and (7b) on the side of the common foil (4) from which the metering element (8) extends downwards. The sample pick-up and metering device (1) can be fixed in this state by additional attachment elements that are not shown here, for example by detent members on one or both parts of the support or by fixing with adhesive. A liquid compartment (5a) or (5b) can for example be opened in this state by moving the two parts of the support (7a) and (7b) relative to one another such that the foil (4) is pulled off at least in the area of the discharge tongue (6) of a liquid compartment and the liquid contained therein can be released.

Figure 4A:
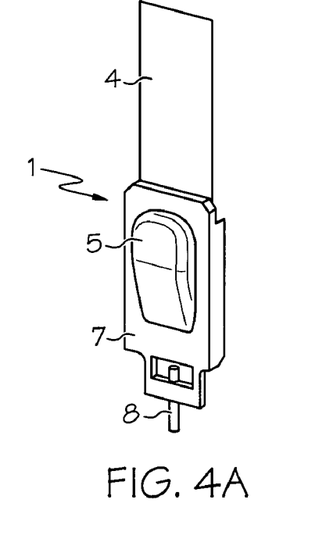
FIGS. 4A-C show views of an embodiment example of an analytical test system according to the invention which comprises a sample pick-up and metering device that has a liquid compartment and a reaction cuvette.
Figure 4B:
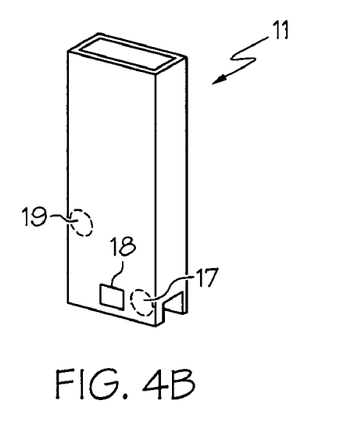
Figure 4C:
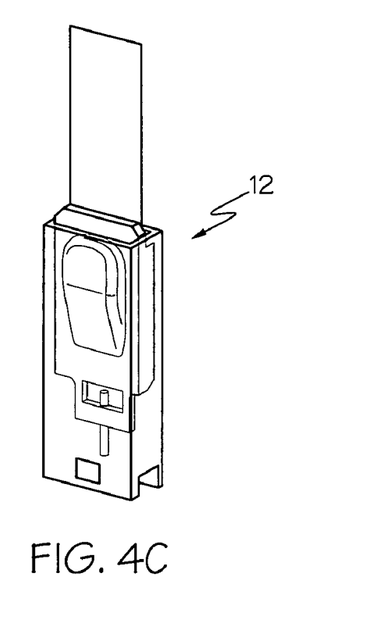

FIGS. 4A-C show views of an embodiment example of an analytical test system (12) according to the invention which comprises a sample pick-up and metering device (1) according to FIG. 1 (see FIG. 4A) and a reaction cuvette (11) (see FIG. 4B). In the case shown the reaction cuvette (11) is equipped with a detection device (18) in the form of a transparent measuring window to detect a characteristic measured quantity for the analyte by means of optical methods. The bottom area of the reaction cuvette (11) additionally contains a first dry chemistry reagent (17) and contains a second dry chemistry reagent (19) in an area that is further towards the top. These reagents can be attached to these sites on the wall of the reaction cuvette (11) by various methods known to a person skilled in the art for example by attaching a matrix or fleece material impregnated with reagents or by applying and subsequently drying a reagent solution during the manufacturing process of the reaction cuvette (11). After the sample liquid to be examined such as a blood sample has been picked up in the metering element (8) of the sample pick-up and metering device (1), the reaction cuvette (11) and the sample pick-up and metering device (1) can now be brought together to form an analytical test system (12) in order to carry out the analyte determination (see FIG. 4C). For this purpose the reaction cuvette (11) and the sample pick-up and metering device (1) can optionally have guide or attachment elements such as grooves, slots or latching connections which facilitate the assembly of the two parts and/or fix the two parts in a fixed spatial position relative to one another which can increase the user friendliness as well as the operating reliability. In this state in which neither the sample liquid nor the liquid contained in the liquid compartment (5) are introduced into the reaction cuvette (11), a first optical measurement can be carried out in the area of the detection device (18) for example as a blank value determination. The liquid contained in the liquid compartment (5) which is for example a buffer solution is released by pulling off the foil (4) upwards and flows into the reaction cuvette (11). In the reaction cuvette it comes, on the one hand, into contact with the sample liquid contained in the metering element (8) and mixes with this sample liquid as a result of which this liquid is prepared and diluted for the analyte determination in the reaction cuvette (11). On the other hand, the first dry chemistry reagent (17) can be dissolved by the released liquid to form a reaction mixture which as a total is composed of the sample liquid, the liquid that was previously contained in the liquid compartment (5) and the substances of the first dry chemistry reagent (17). The foil (4) can in this case be removed manually or by means of a mechanical device which grips the upwards protruding end of the foil (4) and moves it upwards by a certain distance by means of an appropriate control. In this reaction mixture it is now possible for one or even more detection reactions of a multistep analyte determination to proceed. The reaction mixture can be further mixed for example by means of a magnetic stirrer bar present in the cuvette (11). Since at this time the reaction mixture should not yet come into contact with the second dry chemistry reagent (19), the position of this second dry chemistry reagent (19) in the reaction cuvette (11) should be selected with regard to the liquid level of the reaction mixture and taking into account the stirrer movement such that the liquid level remains below the position of the second dry chemistry reagent (19) even when stirred gently. At this time a second optical measurement can for example be carried out in the area of the detection device (18) for example as a reference value determination. In a subsequent step the peripheral regions of the liquid surface can then be moved upwards by for example increasing the stirring rate such that the reaction mixture now comes into contact with the second dry chemistry reagent (19) which is thus added to the reaction mixture. This enables one or more additional detection reactions of a multistep analyte determination to proceed which require the substances contained in the second dry chemistry reagent (19). At this time a third optical measurement can for example be carried out in the area of the detection device (18) for example as a determination of the measured value. A characteristic measured quantity for the analyte can be determined from the measured values of the optical measurement on the basis of which the concentration of the analyte in the sample liquid can be determined if other parameters such as the volumes of the liquids involved are known.

Figure 5A:
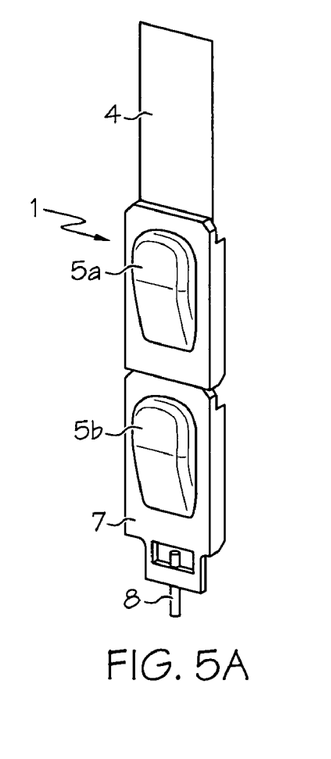
FIGS. 5A-C show views of an embodiment example of an analytical test system according to the invention which comprises a sample pick-up and metering device that has two liquid compartments and a reaction cuvette.
Figures 5B, 5C:
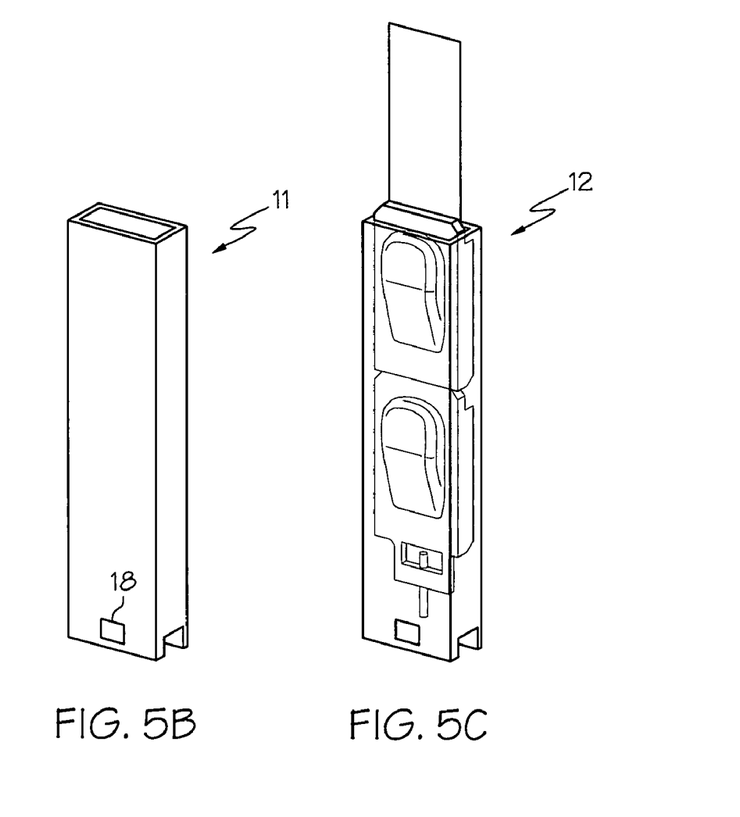

FIGS. 5A-C show views of an embodiment example of an analytical test system (12) according to the invention which comprises a sample pick-up and metering device (1) according to FIG. 2 (see FIG. 5A) and a reaction cuvette (11) (see FIG. 5B). In the case shown the reaction cuvette (11) is equipped with a detection device (18) in the form of a transparent measuring window to detect a characteristic measured quantity for the analyte by means of optical methods.

After the sample liquid to be examined such as a blood sample has been taken up into the metering element (8) of the sample pick-up and metering device (1), the reaction cuvette (11) and the sample pick-up and metering device (1) can be brought together to form an analytical test system (12) in order to carry out the analyte determination (see FIG. 5C). In this state in which neither the sample liquid nor the liquid contained in the liquid compartment (5a, 5b) have been introduced into the reaction cuvette (11), it is now possible to carry out a first optical measurement in the region of the detection device (18) for example as a blank value determination. The liquid contained in the second liquid compartment (5b) which is for example a first reagent solution is released and flows into the reaction cuvette (11) by pulling off the foil (4) upwards by a certain distance. In the reaction cuvette (11) the reagent solution now comes into contact, on the one hand, with the sample liquid contained in the metering element (8) by which means the sample liquid is prepared, diluted and mixed with the substances contained in the first reagent solution to form a reaction mixture for the analyte determination in the reaction cuvette (11). One or also more detection reactions of a multistep analyte determination can now proceed in this reaction mixture. The reaction mixture can be mixed further for example by means of a magnetic stirrer rod present in the cuvette (11) which ensures a good intermixing of the components of the reaction mixture. At this time a second optical measurement can for example be carried out in the region of the detection device (18) such as a reference value determination. In a subsequent step the foil (4) can be removed further by a certain distance to release the liquid contained in the first liquid compartment (5a) which is for example a second reagent solution that flows into the reaction cuvette (11) by means of which the reagents contained therein are added to the reaction mixture. As a result one or also more additional detection reactions of a multistep analyte determination which require these substances contained in the second reagent solution can occur. At this time a third optical measurement can for example be carried out in the region of the detection device (18) for example as a determination of a measured value. A characteristic measured quantity for the analyte can be determined from the measured values of the optical measurements on the basis of which the concentration of the analyte in the sample liquid can be determined when other parameters such as the volumes of the liquids involved are known. In this embodiment the foil (4) can be present folded from the bottom towards the upper region in order to enable a controlled sequential opening of the individual liquid compartments (5a, 5b). The other embodiments described in connection with FIG. 4 also apply accordingly to an analytical test system according to FIG. 5.

Figure 6A:
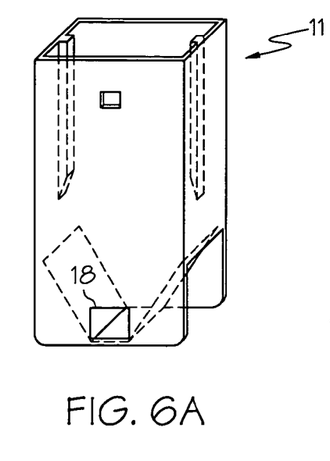
FIGS. 6A-B show views of a further embodiment example of an analytical test system according to the invention which comprises a sample pick-up and metering device that has two liquid compartments and a reaction cuvette.
Figure 6B:
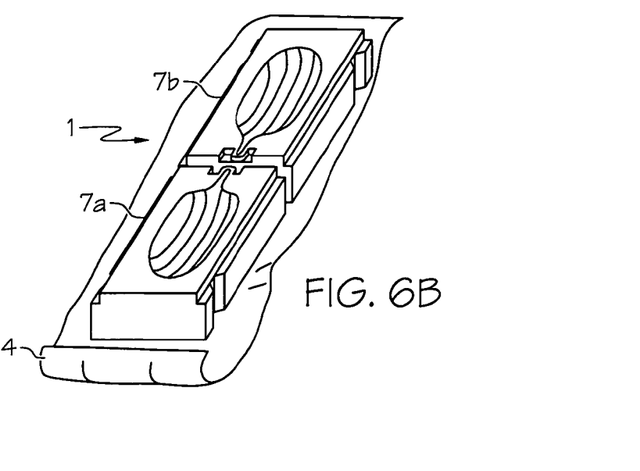

FIGS. 6A and 6B show views of another embodiment of an analytical test system according to the invention which comprises a sample pick-up and metering device (1) according to FIG. 3 (see FIG. 6B) and a reaction cuvette (11) (see FIG. 6A). In the case shown the reaction cuvette (11) is equipped with a detection device (18) in the form of a transparent measuring window to detect a characteristic measured quantity for the analyte by means of optical methods. The reaction cuvette (11) can as shown optionally have guide or attachment elements such as grooves or slots which simplify the assembly of the reaction cuvette (11) and sample pick-up and metering device (1) and/or specify defined directions of movements of the parts relative to one another by means of which the convenience and operating reliability can be increased.

Figure 7A:
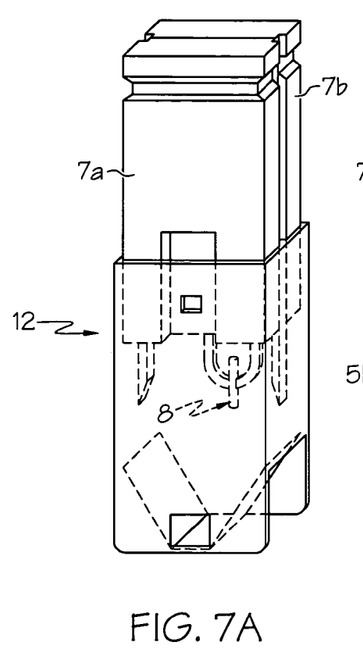
FIGS. 7A-C show views of an inventive analytical test system according to FIG. 6 at various process stages when carrying out an analyte determination.
Figure 7B:
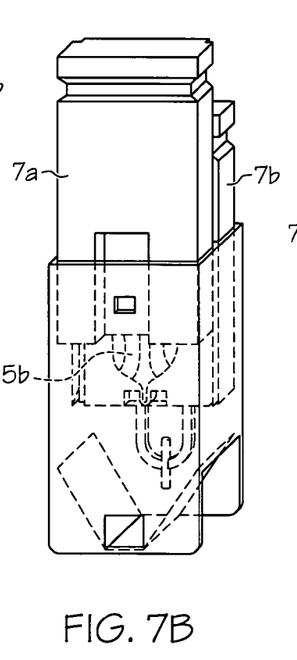
Figure 7C:
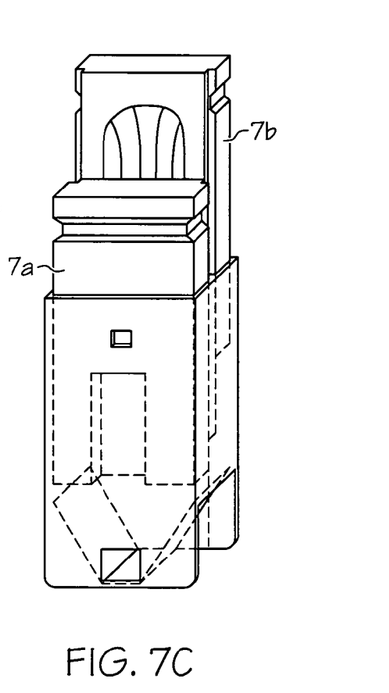

FIGS. 7A-C show views of an inventive analytical test system according to FIG. 6 at various stages in the process of carrying out an analyte determination.

A sample pick-up and metering device from which the metering element (8) extends downwards can be prepared by bringing together the two support parts (7a) and (7b) on the side of the common foil. Since the two support parts (7a) and (7b) are flexibly linked together by the common foil, the sample pick-up and metering device can thus be brought into a form in which it can be inserted into the reaction cuvette in order to carry out an analyte determination. The sample pick-up and metering device can be fixed in this state by additional attachment elements that are not shown here for example by detent members on one or both parts of the support or by attachment by means of releasable adhesive connections. The liquid compartments (5a) or (5b) can for example be opened by displacing the two support parts (7a) and (7b) relative to one another such that the foil is pulled off at least in the region of a discharge tongue of a liquid compartment and the liquid contained therein can be released.

In order to carry out an analyte determination the sample to be examined, for example a blood sample, is taken up in the metering element (8) of the sample pick-up and metering device. Subsequently the reaction cuvette and the sample pick-up and metering device are brought together as previously described to form an analytical test system (12). In this state in which neither the sample liquid nor the liquid contained in the liquid compartments (5a) and (5b) have been introduced into the reaction cuvette, a first optical measurement can now be carried out in the region of the detection device for example as a blank value determination. By pressing down the second support part (7b) during which the first support part (7a) retains its original position (see FIG. 7B), the liquid contained in the second liquid compartment (5b) which is for example a first reagent solution is released and flows into the reaction cuvette. The second liquid compartment (5b) is opened by a downwards movement of the second support part (7b) which removes the common foil that is attached to the first support part (7a) in the region of the discharge tongue of the second liquid compartment (5b). The first reagent solution that is contained therein now comes into contact with the sample liquid contained in the metering element (8) which prepares, dilutes and mixes this liquid with the substances contained in the first reagent solution to form a reaction mixture for the analyte determination in the reaction cuvette. One or also more detection reactions of a multistep analyte determination can now proceed in this reaction mixture. The reaction mixture can be mixed further for example by means of a magnetic stirrer rod present in the cuvette which ensures a good intermixing of the components of the reaction mixture. At this time a second optical measurement can for example be carried out in the region of the detection device such as a reference value determination. In a subsequent step the liquid contained in the first liquid compartment which is for example a second reagent solution can be released by pressing down the first support part (7a) during which the second support part (7b) retains its original position or is returned to this position (see FIG. 7C). This liquid flows into the reaction cuvette whereby the reagents contained therein are added to the reaction mixture. As a result one or also more additional detection reactions of a multistep analyte determination which require these substances contained in the second reagent solution can occur. At this time a third optical measurement can for example be carried out in the region of the detection device for example as a determination of a measured value. A characteristic measured quantity for the analyte can be determined from the measured values of the optical measurements on the basis of which the concentration of the analyte in the sample liquid can be determined when other parameters such as the volumes of the liquids involved are known. The relative movement of the two support parts (7a) and (7b) can be carried out by instrumentation devices which are appropriately controlled. For this purpose the upper region of the support parts (7a) and (7b) can be designed as shown for example in FIGS. 7A-C and for example have grooves in which an instrument device engages, and the appropriate displacement movements of the support parts relative to one another can be achieved by lifting or pressing down one or both support parts.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is

1. A method for determining an analyte in a liquid sample comprising:
    a) providing an analytical test system comprising:
        a sample pick-up and metering device comprising:
            a metering element that picks up and retains a defined volume of the liquid sample,
            a support which contains at least one closed liquid compartment in which a defined volume of a liquid is contained, wherein
                the support, the liquid compartment, and the metering element form one constructional unit, and
                the metering element is fixedly connected to the support, and
        a reaction cuvette;
    b) contacting the metering element with the liquid sample to be analyzed such that the defined volume of the liquid sample remains in the metering element;
    c) introducing the sample pick-up and metering device into the reaction cuvette;
    d) opening at least one liquid compartment on the support such that the liquid contained in this liquid compartment flows into the reaction cuvette and comes there into contact with the liquid sample contained in the metering element in such a manner that the liquid sample from the metering element is provided in the reaction cuvette and a reaction mixture is formed; and
    e) determining the analyte on the basis of a characteristic measured quantity for the analyte.

2. The method according to claim 1 further comprising adding reagents for the determination of the analyte and/or intermixing the reaction mixture.

3. The method according to claim 1 further comprising determining the analyte on the basis of a characteristic measured quantity for the analyte by optical detection methods.

4. An analytical test system for determining an analyte in a liquid sample comprising:
    a support including
        a closed liquid compartment in which a defined volume of a liquid is contained, the liquid compartment being closed by a liquid-tight and gas-tight foil that can be pulled off or pierced, and
        a metering element including a capillary that picks up and retains a defined volume of the liquid sample; and
    a reaction cuvette defining a volume that receives the support;
    wherein the liquid compartment is configured to be opened to release the liquid contained in the liquid compartment into the reaction cuvette to mix with the liquid sample and facilitate analyte determination.

5. A sample pick-up and metering device comprising:
    a metering element; and
    a support which contains at least one closed liquid compartment in which a defined volume of a liquid is contained, wherein
        the metering element includes a capillary with two free openings that picks up and retains a defined volume of liquid sample and forms one constructional unit with the support and the liquid compartment, and
        the liquid compartment is closed by a liquid-tight and gastight foil, which when pulled causes the defined volume of the liquid contained in the liquid compartment to come into contact and mix with the defined volume of liquid sample contained in the metering element.

6. The sample pick-up and metering device according to claim 5, wherein the support is configured such that after opening the liquid compartment, the liquid contained in the liquid compartment comes into contact with and is mixed with the defined volume of the liquid sample contained in the metering element.

7. The sample pick-up and metering device according to claim 5, wherein at least one liquid contained in the liquid compartment is a buffer solution or diluent solution or a reagent solution.

8. The sample pick-up and metering device according to claim 5, wherein two or more liquid compartments that are separate from one another are present on the support.

9. The sample pick-up and metering device according to claim 8, wherein said compartments are opened simultaneously or sequentially.

10. An analytical test system for determining an analyte in a liquid sample comprising:
    a sample pick-up and metering device according to claim 5, and
    a reaction cuvette.

11. The analytical test system according to claim 10 further comprising a mixing device.

12. The analytical test system according to claim 10, wherein the reaction cuvette contains one or more devices which enable a determination of the analyte in the reaction cuvette.

13. The analytical test system according to claim 10, wherein the specific reagent liquids required to determine the analyte are contained in one or more liquid compartments on the support of the sample pick-up and metering device.

14. The analytical test system according to claim 10, wherein the specific reagents required to determine the analyte are contained in the reaction cuvette.

15. The analytical test system according to claim 14, wherein said reagents are in a dry chemistry form.

16. The analytical test system according to claim 10, wherein the analyte is determined by sequential detection reactions.

17. The analytical test system according to claim 10, wherein the analyte is haemoglobin A1 c and said liquid sample is blood.

* * * * *